US011915412B2

(12) United States Patent
Zagorchev et al.

(10) Patent No.: US 11,915,412 B2
(45) Date of Patent: Feb. 27, 2024

(54) CORTICAL MALFORMATION IDENTIFICATION

(71) Applicant: KONINKLIJKE PHILIPS N.V., Eindhoven (NL)

(72) Inventors: Lyubomir Georgiev Zagorchev, Burlington, MA (US); Fabien Wenzel, Hamburg (DE); Martin Bergtholdt, Hamburg (DE); Houchun Hu, Burlington, MA (US); Jeffrey Miller, Burlington, MA (US); Carsten Meyer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 139 days.

(21) Appl. No.: 16/475,480

(22) PCT Filed: Jan. 3, 2018

(86) PCT No.: PCT/EP2018/050089
§ 371 (c)(1),
(2) Date: Jul. 2, 2019

(87) PCT Pub. No.: WO2018/127499
PCT Pub. Date: Jul. 12, 2018

(65) Prior Publication Data
US 2019/0347795 A1 Nov. 14, 2019

Related U.S. Application Data

(60) Provisional application No. 62/443,061, filed on Jan. 6, 2017.

(51) Int. Cl.
G06T 7/00 (2017.01)
G16H 30/40 (2018.01)
G06T 19/20 (2011.01)

(52) U.S. Cl.
CPC ............ G06T 7/0012 (2013.01); G06T 19/20 (2013.01); G16H 30/40 (2018.01);
(Continued)

(58) Field of Classification Search
CPC ......... G06T 2207/30016; G06T 7/0012; G06T 2207/10088
See application file for complete search history.

(56) References Cited

U.S. PATENT DOCUMENTS 8,031,919 B2 * 10/2011 Eskildsen ............... G06K 9/48
382/128
9,530,206 B2 12/2016 Liu et al.
(Continued)

OTHER PUBLICATIONS

Timonen-Soivio, Laura et al. "The association between congenital anomalies and autism spectrum disorders in a Finnish national birth cohort." Developmental medicine and child neurology vol. 57,1 (2015): 75-80. doi:10.1111/dmcn.12581 (Year: 2015).*
(Continued)

Primary Examiner — Ross Varndell

(57) ABSTRACT

A cortical malformation identification method includes quantitatively evaluating, using a processor of a computer that includes the processor and a memory, digital image data from a magnetic resonance imaging (MRI) scan on a cerebral cortex to produce quantified scan data. The method also includes automatically detecting a cortical malformation based on the quantified scan data. An image of the cerebral cortex may be color-coded so that the cortical malformation is shown in a different color than the remainder of the cerebral cortex in the image, based on the quantified scan data. Additionally or alternatively, a 3-dimensional representation of the cerebral cortex may be mapped to the quantified scan data to produce a mapped image of the cerebral cortex including the detected cortical malformation.

18 Claims, 9 Drawing Sheets

(52) U.S. Cl.
CPC ............. *G06T 2207/10088* (2013.01); *G06T 2207/30016* (2013.01); *G06T 2210/41* (2013.01); *G06T 2219/028* (2013.01); *G06T 2219/2012* (2013.01)

(56) References Cited

U.S. PATENT DOCUMENTS

| | | |
|---|---|---|
| 2005/0148859 A1 | 7/2005 | Miga et al. |
| 2012/0327075 A1 | 12/2012 | Zagorchev et al. |
| 2013/0066189 A1 | 3/2013 | Zagorchev et al. |
| 2013/0259346 A1 | 10/2013 | El-Baz et al. |
| 2015/0289779 A1* | 10/2015 | Fischl .................. A61B 5/0037 600/410 |
| 2016/0166192 A1 | 6/2016 | Lepore et al. |
| 2016/0306023 A1 | 10/2016 | Zagorchev et al. |
| 2017/0032520 A1* | 2/2017 | Nitzken .................. G06T 7/0012 |

OTHER PUBLICATIONS

Ruben I. Kuzniecky, "MRI in cerebral developmental malformations and epilepsy," Magnetic Resonance Imaging, vol. 13, Issue 8, 1995, pp. 1137-1145, ISSN 0730-725X, https://doi.org/10.1016/0730-725X(95)02024-N. (Year: 1995).*

Kim Jaeil et al "3D Shape Analysis of the Brain's Third Ventricle Using a Midplane Encoded Symmetric Template Model" Computer Methods and Programs in Biomedicine, vol. 129, Feb. 28, 2016 p. 51-62.

Manhua Liu et al "Ensemble Sparse Classification of Alzheimer's Disease" Neuroimage, Apr. 2, 2012 p. 1-29.

Aronica, E., A. J. Becker, et al. (2012). "Malformations of cortical development." Brain Pathology 22(3): 380-401.

Macdonald "Automated 3D Extraction of Inner and Outer Surfaces of Cerebral Cotex From MRI" Neuroimage, 12 p. 340-256, 2000.

Anderson M. Winkler et al., "Measuring and comparing brain cortical surface area and other areal quantities" Neuroimage, 61 (2012) p. 1428-1443.

Kiho Im et al.,Quantification and Discrimination of Abnormal Sulcal Patterns in Polymicrogyria Cerebral Cortex Dec. 2013;23:3007-3015.

Anders M. Dale et al.,Cortical Surface-Based Analysis I. Segmentation and Surface Reconstruction Neuroimage, 9 p. 179-194 (1999).

Dr.P.Subashini et al., "A Study on Detection of Focal Cortical Dysplasia Using MRI Brain Images" Journal of Computer Applications, vol. IV, Issue 1, 2011.

O. Colliot et al., "Segmentation of Focal Cortical Dysplasia Lesions on MRI Using Level Set Evolution" Neuroimage, 32 p. 1621-1630 (2006).

International Search Report from PCT/EP2018/050089 dated Mar. 27, 2018.

* cited by examiner

Top view

Front view 701  702

CORTICAL MALFORMATION IDENTIFICATION

CROSS REFERENCE TO RELATED APPLICATIONS

This application is a U.S. national phase application of International Application No. PCT/EP2018/050089 filed on Jan. 3, 2018, which claims the benefit of U.S. Provisional Application Ser. No. 62/443,061 filed on Jan. 6, 2017 and is incorporated herein by reference.

BACKGROUND

The cerebral cortex is the outermost layer of tissue that covers white matter tracts in the brain. The cerebral cortex has a dark grey appearance on standard magnetic resonance imaging (MRI) scans. The relatively thin layer of tissue of the cerebral cortex is the main information processing center in the brain.

Cortical malformations such as Taylor's focal cortical dysplasia, architectural dysplasia, and/or cytoarchitectural dysplasia are abnormalities of the cerebral cortex that arise as a consequence of an interruption to a normal process of cortical formation. The human cerebral cortex develops its basic structure gradually, beginning with proliferation and differentiation of neurons, which then gradually migrate and position themselves in the cerebral cortex. Abnormalities during the normal process cause a disruption of neuronal activity and predispose the human with the cerebral cortex to a variety of clinical consequences, the most common of which is epileptic seizures.

FIG. 1A illustrates a standard MRI scan of a "normal" cerebral cortex 100. FIG. 1B illustrates a standard MRI scan of an "abnormal" cerebral cortex 110 affected by focal cortical dysplasia. In FIGS. 1A and 1B, the cerebral cortexes 100 and 110 are shown with a dark grey appearance. In FIG. 1B the "fuzzy" area identified by the arrow is the area of the abnormal cerebral cortex 110 affected by the focal cortical dysplasia, i.e., is the abnormal cortical formation (cortical malformation) 111.

BRIEF DESCRIPTION OF THE DRAWINGS

The example embodiments are best understood from the following detailed description when read with the accompanying drawing Figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
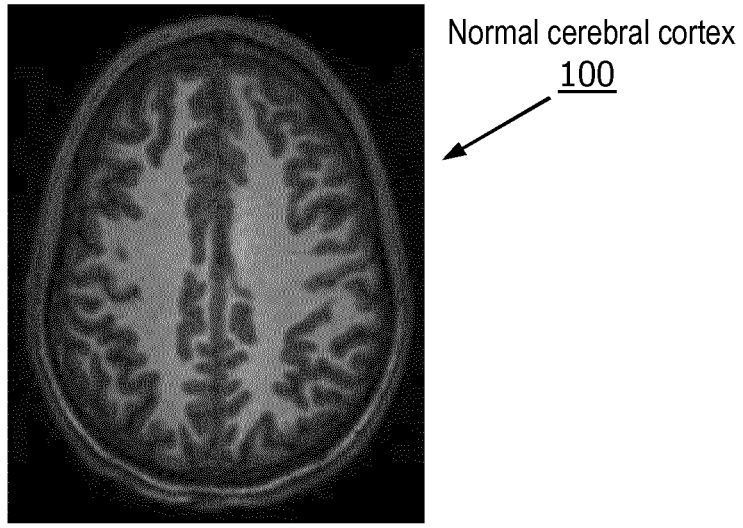
FIG. 1a is a view of a standard MRI scan of a "normal" cerebral cortex.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted to avoid obscuring the description of the representative embodiments. Nonetheless, systems, devices, materials and methods that are within the purview of one of ordinary skill in the art are within the scope of the present teachings and may be used in accordance with the representative embodiments. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Figure 2:
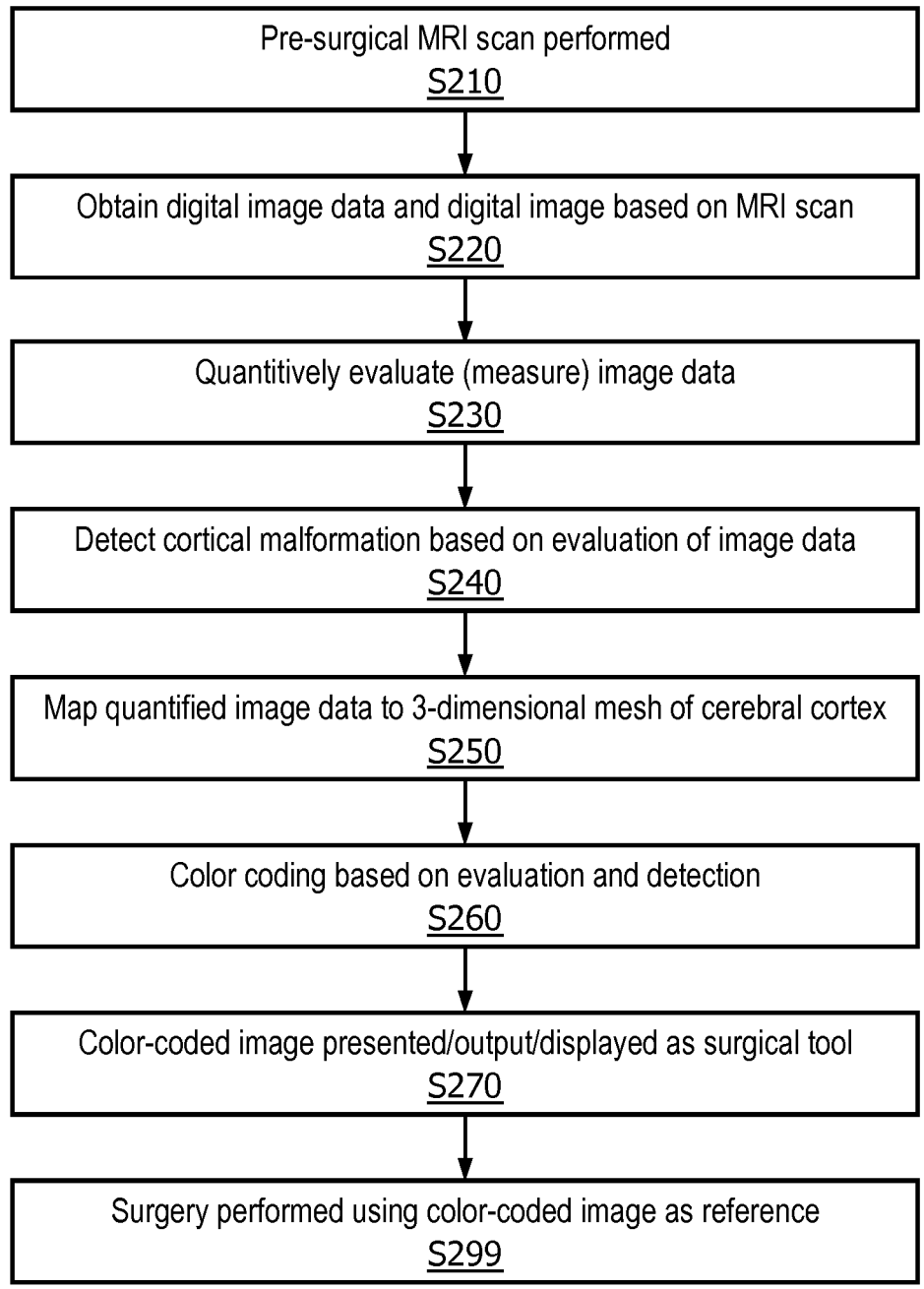
FIG. 2 is a view of a process for cortical malformation identification, in accordance with a representative embodiment of the present disclosure.

FIG. 2 is a view of a process for cortical malformation identification, in accordance with a representative embodiment of the present disclosure. In FIG. 2, the process starts at S210 when a pre-surgical magnetic resonance imaging scan is performed. Of course, a magnetic resonance imaging scan performed for cortical malformation identification does not have to be pre-surgical. Rather, the magnetic resonance imaging scan may be performed in a process that does not result in surgery.

A magnetic resonance imaging scan uses magnets to align and realign hydrogen nuclei (protons) in water molecules in a subject (e.g., human) being imaged. Strong magnetic fields are applied to align and realign the proton "spins". Radio frequency (RF) coils then selectively deliver a B1 field in a transmit stage. In a receive stage, the hydrogen atoms return to an original position (i.e., the position before the selective delivery of the B1 field) and emanate a weak radio frequency signal which can be picked up and used to produce images.

Figure 4:
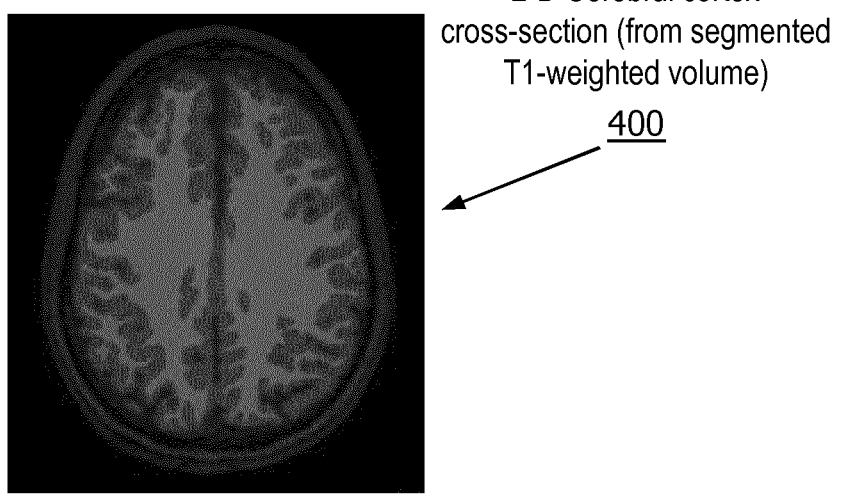
FIG. 4 is a view of a 2-dimensional image of a segmented cerebral cortex for cortical malformation identification, in accordance with a representative embodiment of the present disclosure.
Figure 5:
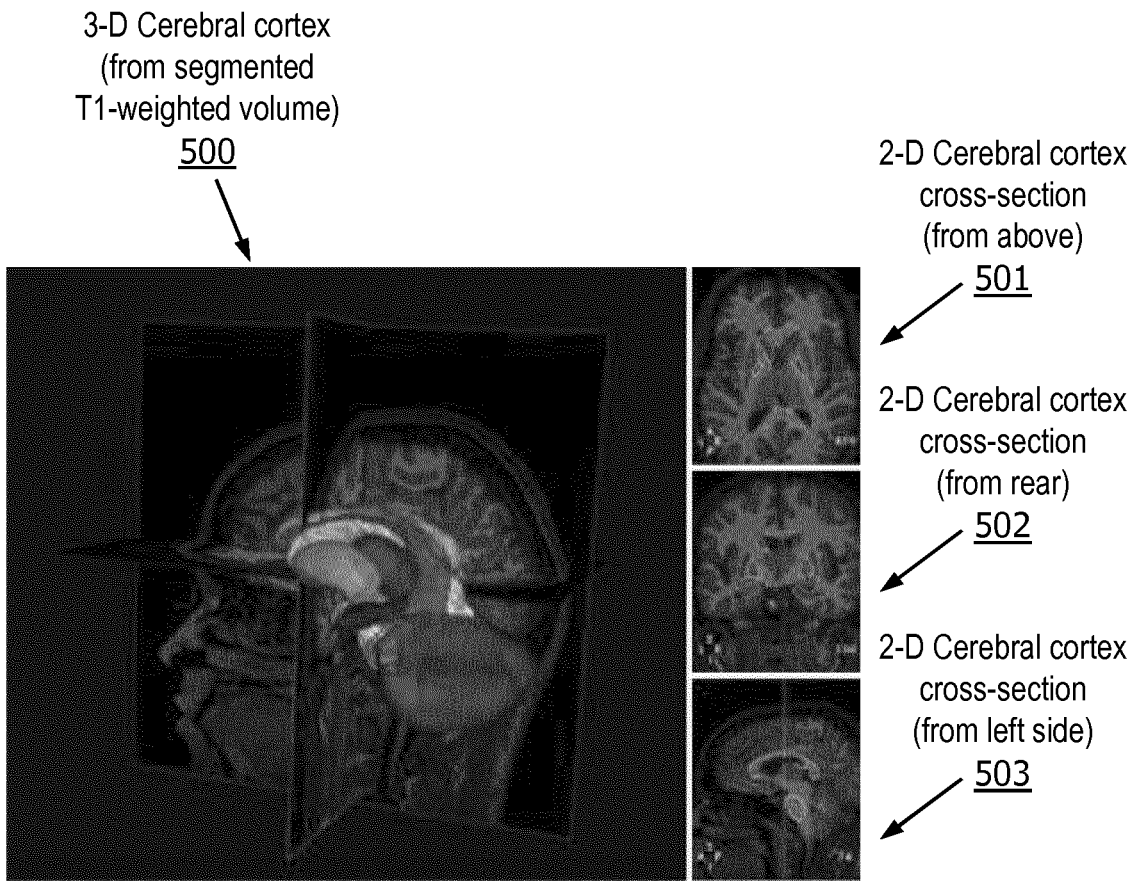
FIG. 5 is a view of a 3-dimensional image and several 2-dimensional images of a segmented cerebral cortex for cortical malformation identification, in accordance with a representative embodiment of the present disclosure.
Figure 6:
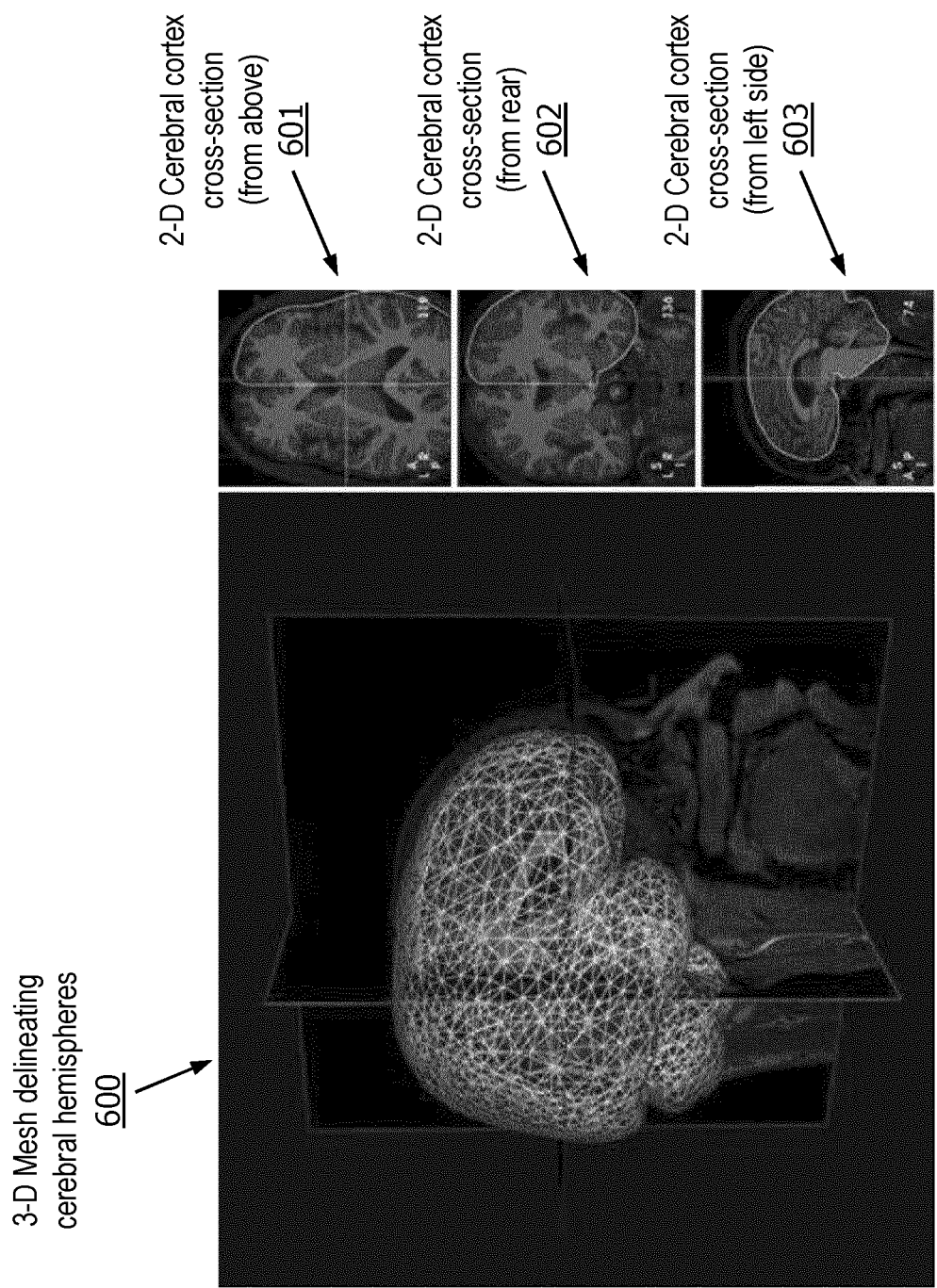
FIG. 6 is a view of a 3-dimensional image and several 2-dimensional images of a segmented cerebral cortex with a superimposed mesh for cortical malformation identification, in accordance with a representative embodiment of the present disclosure.

Deformable segmentation followed by tissue classification can be used to segment the cerebral cortex in the pre-operative magnetic resonance imaging scan at S210. The scan may be a high-resolution scan. A result of segmentation of the cerebral cortex (green) is shown in FIGS. 4, 5 and 6. The segmentation of the cerebral cortex is rapid, fully-automatic, and eliminates all user interaction. After the cerebral cortex is obtained, the inner and outer cortical boundaries can be represented as triangular meshes. To visualize the concept, a 3-dimensional mesh delineating the cerebral hemispheres is illustrated in FIG. 6 as described below.

In FIG. 4, a 2-dimensional cerebral cortex cross-section image 400 is shown. The 2-dimensional cerebral cortex cross-section image 400 of a cerebral cortex is from a segmented T-1 weighted volume. In FIG. 4, the cortex is shown in green.

A T-1 weighted volume is used for magnetic resonance imaging, and demonstrates differences in the T-1 relaxation times of tissues. The T-1 relaxation time is reflected by when 63% of the longitudinal magnetization of protons is recovered after protons (spins) from the aligned external field (B0) are put into the transverse plane by a radio frequency pulse. During the process of T-1 relaxation, the protons reorient resulting in recovery of longitudinal magnetization. T-1 relaxation is measured using a time constant called T-1. T-1 is usually reported in milliseconds. A T-1 weighted imaging is used to differentiate anatomical structures of cerebral cortexes mainly based on T-1 values. Tissues with high fat content (e.g. white matter) appear bright and compartments filled with water appears dark. The T-1 weighting is used in the magnetic resonance imaging described herein.

In FIG. 5, four separate images are shown together for the same 3-dimensional cerebral cortex 500 from a segmented T-1 weighted volume. In the left image, segmentation is shown to include visually bisecting the 3-dimensional cerebral cortex with three planes, i.e., a horizontal plane and two vertical planes. The vertical segmenting planes include one lateral first plane that passes from one side of the head to the other, and a second plane that passes from the front of the head to the rear. The second plane is visually provided halfway or approximately halfway between the sides of the head of the patient/subject, with the assumption that the head of the patient/subject is substantially symmetrical. The result of the segmentation shown in the left image is eight (8) separate sections in the 3-dimensional cerebral cortex In FIG. 5, the three 2-dimensional images 501, 502, 503 to the right are a 2-dimensional axial cross-section image 501, a 2-dimensional coronal cross section image 502, and a 2-dimensional sagittal cross section image 503. All three of the 2-dimensional images 501, 502, 503 are projections onto the three bisecting planes shown in the 3-dimensional image to the left.

In FIG. 6, a superimposed 3-dimensional mesh delineates the cerebral hemispheres 600. The inner and outer boundaries of the cerebral cortex are represented as similar triangular surfaces. Signal intensity between corresponding triangular surfaces of the inner and outer boundaries can be measured during the scan at S210. In particular, signal intensity values are measured normal to, and pointing inward/outward, from the inner or outer cortical surface, of the mesh.

In FIG. 6, the three 2-dimensional images 601, 602, 603 to the right are a 2-dimensional axial cross-section image 601, a 2-dimensional coronal cross-section image 602, and a 2-dimensional sagittal cross-section image 603. All three of the 2-dimensional images 601, 602, 603 are the three bisecting planes shown in the 3-dimensional image to the left. As described below, the data used for the images in FIG. 6 is from the measurements of signals normal to the inner and outer cortical surfaces of the mesh shown in the 3-dimensional image to the left.

Returning to FIG. 2, at S220, digital image data and a digital image are obtained based on the MRI scan performed at S210. As described already, the digital image data and digital image reflect signal intensities for signals from the patient/subject being subjected to the scan at S210. That is, the MRI scan at S210 may result in generation at S220 of one or more images of a cerebral cortex similar or identical to images resulting from conventional MRI scans of cerebral cortexes.

At S230, the image data is measured and quantitatively evaluated. The image data is measured using pixel (in 2-D) or voxel (in 3-D) values reflective of the signal intensity at corresponding locations along the contour (in 2-D) or triangle (in 3-D) normals defined by the meshes, respectively. Triangle normals are further explained below. In turn, the intensity value (at a pixel or a voxel) reflects the corresponding radio frequency signals from the patient/subject. For example, in a greyscale image up to 256 different possible intensity values can be indicated by/in 8-bits (i.e., a byte). In the example using greyscale, a pixel or voxel may be designated as black with a zero (0) value, and a pixel or voxel may be designated as white with a value of two hundred fifty-five (255). Intensity ranges other than 256 values can be used.

The pixel or voxel values in the image data at S230 reflect the signal strength of radio frequency signals emanating from, e.g., hydrogen, atoms subject to the magnetic resonance scan including the selectively delivered B1 field. Of course, the signal strength of the radio frequency signals is not digital, and therefore is not typically contained to the finite number of pixel or voxel values reflected in image data. Accordingly, signal strength may be divided into ranges that are either predetermined or dynamically determined during a magnetic resonance imaging scan. The number of ranges may be equal to the number of potential pixel or voxel values. Accordingly, the measuring of signals or image data described herein reflects a measurement of individual signal strength for different radio frequency signals represented by individual pixels or voxels used to generate the image data and digital image.

The quantitative analysis at S230 is more complex than the measurements of pixel or voxel values reflective of signal strength. For example, quantitative analysis at S230 may involve a procedure using measured readings for multiple pixel or voxel values. As an example, when pixels are arranged in a grid of linear rows and columns, an interior pixel (i.e., not at an edge of the grid) may be considered a center pixel surrounded immediately by eight (8) other pixels in 2-D. The eight other pixels would be pixels on each side (i.e., to the left and right), above and below, and diagonally to the upper right, lower right, upper left, and lower left. In 3-D, voxels are surrounded immediately by twenty six (26) other voxels. In general, any representation or analysis in 2-D can be extended to 3-D by adding one more spatial dimension.

Quantitative analysis in 3-D at S230 may be performed along triangle normals as defined by the meshes representing the inner and outer cortical boundaries. The average at a given voxel location along a triangle normal may be estimated by using immediately surrounding voxels, or voxels in a pre-defined local neighborhood. Such an average thus is an area average of voxel values including the center voxel and the values of the immediately surrounding neighbors. The averaging process can be performed for all voxels along triangle normals within certain distance of the cortical surface. Alternatively, the average may be an average of voxel values including the voxel centered on the triangle normals and the values of voxels from a pre-defined spatial template surrounding the center voxel (for example, a 3×3×3 cube, or a sphere).

Additionally, signal values may be taken over time for the same pixels. A time series of pixel values from magnetic resource images may show a progression of a cortical malformation. Similarly, averages of values for a single pixel or voxel from several images taken at different times in a single magnetic resonance imaging session (e.g., during S210) may show a better representation of the actual signal value for each corresponding pixel.

Cortical malformations can thus be detected and measured as the average intensity value of pixels in the magnetic resonance image. Analysis other than averages may be performed on intensity values, so long as the analysis differentiates between normal and abnormal tissue shown in the magnetic resonance image. As used herein, the word "intensity" refers to signal intensity or signal strength. This is reflected in the greyscale contrast shown in the images output from a magnetic resonance imaging system. In the images, black may be referred to as "hypointense" due to the low signal intensity, and white may be referred to as "hyperintense" due to the high signal intensity.

Figure 1B:
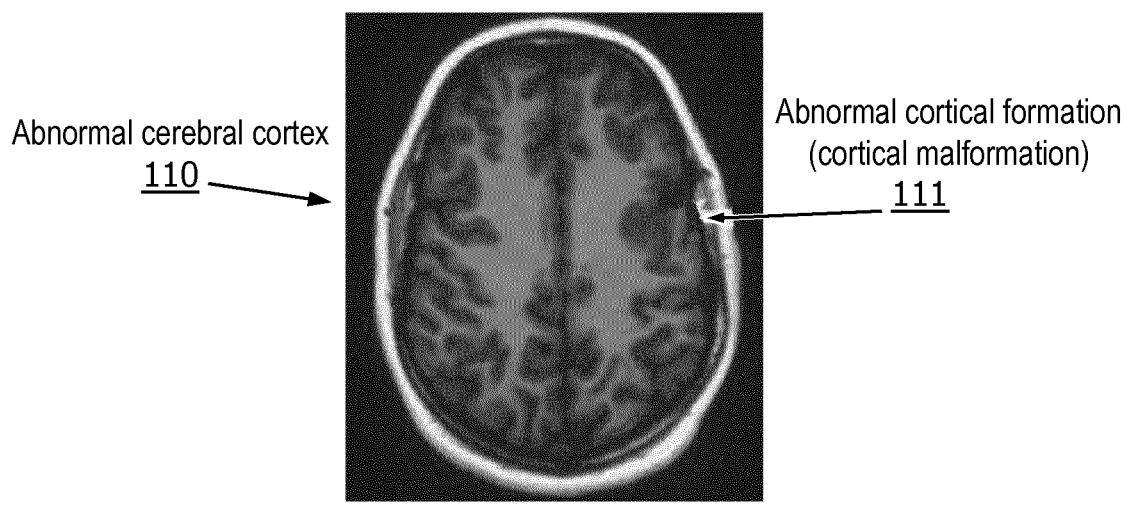
FIG. 1b is a view of a standard MRI scan of an "abnormal" cerebral cortex.

In a greyscale image output from a magnetic resonance imaging system, the abnormal tissue appears as fuzziness around the cortex as shown. This fuzziness is shown in FIG. 1B as the abnormal cortical formation (cortical malformation) 111. At S230, this fuzziness is measured and differentiated from other areas in the magnetic resonance image. As described herein, averages or other types of analytic results (e.g. geometric differences, etc.) derived from the quantitative evaluation of cortical malformations at S230 may also enable accurate post-processing differentiation of disease type, as well as correlation of symptoms with outcome.

At S240, the cortical malformation is detected based on the evaluation of S240. That is, the intensity of radio frequency signals from similar areas of a cerebral cortex will be similar, whereas intensity of radio frequency signals from dissimilar areas of a cerebral cortex will typically be dissimilar. Thus, the average intensity values of radio frequency signals from the region of the cortical malformation will be dissimilar to the average intensity values of radio frequency signals from other regions, or the same region in normal healthy subjects. At S240, the dissimilarity is used to distinguish the cortical malformation from the remainder of the cerebral cortex. Furthermore, the dissimilarity maybe based on any other form of analytical derivative obtained from intensity values or their local averages.

Pixel or voxel values of the region of the cortical malformation may be similar for different patients/subjects with cortical malformations. Accordingly, absolute values of the average pixel or voxel values from magnetic resonance images may be usable to perform the detection at S240. Alternatively, differences between intensity values of the region of the cortical malformation and other regions may be similar for different patients/subjects with cortical malformations. Accordingly, differences of, e.g., average intensity values, for different regions of the imaged cerebral cortex can be used to detect the cortical malformation at S240.

In an embodiment, an alternative process to perform the detection at S240 utilizes the brain symmetry with respect to the midsagittal plane. This is possible given the focal nature of cortical malformations. Detection of abnormal regions can be accomplished by identifying deviations in averages or other derived quantitative indices based on intensity values or intensity derivatives, between the left and right sides of the brain. An example of another type of derivative that can be used is a Taylor Series Expansion based on signal intensity values.

The image data quantifiably evaluated at S230 may be mapped to a 3-dimensional mesh of the cerebral cortex at S250. The 3-dimensional mesh may be obtained using deformable segmentation. A 3-dimensional mesh is shown in FIG. 6 as delineating the cerebral hemispheres. As noted previously, in FIG. 6, inner and outer boundaries of the cortex are represented as similar triangular surfaces. Examples of obtaining a 3-dimensional mesh using deformable segmentation are provided in U.S. patent application Ser. No. 13/514,731 to ZAGORCHEV et al., filed on Nov. 17, 2010, and in U.S. Patent Application Publication No. 2013-0066189 to ZAGORCHEV et al., published on Mar. 14, 2013, each of which is hereby incorporated by reference in the entirety.

At S250, the quantified image data (i.e. from S230) is mapped to the 3-dimensional mesh of the cerebral cortex obtained at or after S210. That is, a value for each voxel of the quantified image data is mapped to a triangle in the inner and outer boundaries of the 3-dimensional mesh of the cerebral cortex that is obtained in the scan at S210. The 3-dimensional mesh in FIG. 6 is used as a spatial template to define the measurement of signal intensity along mesh triangle normals, so the data resulting from the quantitative evaluation at S230 is, in a sense, adding one or more new (analytic result) value(s) to the original imaging data. The intensity values are measured normal to, and pointing inward/outward, from the inner or outer cortical surface, of the mesh. Once the analysis is performed based on the image data, the resultant analysis values, or calculated measurements, are mapped to and plotted on the triangular meshes representing the inner and/or outer cortex for accurate localization of the malformation.

At S260, the quantified image data is color coded based on the evaluation at S230 and/or detection at S240. The color coding may use a single predetermined color to identify the detected cortical malformation, and a visually contrasting color to identify areas/regions surrounding the cortical malformation. For example, a detected cortical malformation may be shown in pink or red, and the surrounding area/region may be shown in blue or grey. The colorization at S260 is performed by identifying areas of the 3-dimensional mesh with quantified results from S240 that are in an expected range that reflects a cortical malformation. For example, in the instance of 256 potential intensity values, an average value in the range of 30-45 may reflect a cortical malformation, and values outside of the range may reflect a normal cortical formation. Any range may be predetermined, or may be identified dynamically using an algorithm that identifies a region/area with signal intensities divergent from signal intensities of surrounding regions/areas.

At S270, the color-coded image is presented, output and/or displayed, e.g., as a surgical tool. The color-coded image may be output using a printer or an electronic screen. An electronic screen may even be a screen of a surgical navigation system that assists surgeons in navigating anatomy of a patient/subject, or with respect to a surgical instrument. In a surgical navigation system, instruments can be tracked in the 3-dimensional space relative to a malformation. At S299, surgery is performed using the color-coded image as a reference.

3-dimensional surfaces matched with quantified image data can be used to compare the same parametric space of different patients. The same parametric space can be defined by the triangular meshes of the inner and/or outer cerebral cortex. Additionally, different properties of the quantified analysis can be used to describe various properties of detected pathology. For example, standard deviation, length along the normal, profile shape and other properties of the 3-dimensional surfaces of different patients can be described using quantitative analysis.

Figure 7A:
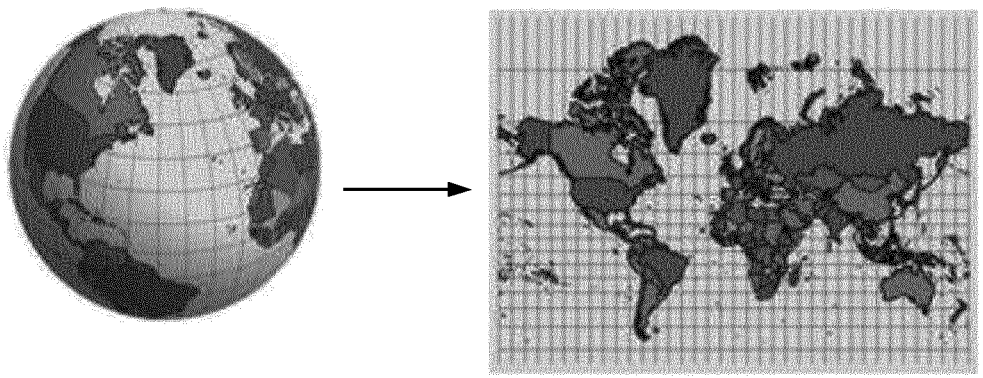
FIG. 7A is a view of an illustrative mapping transformation to map a 3-dimensional spherical surface to a planar rectangle.
Figure 7B:
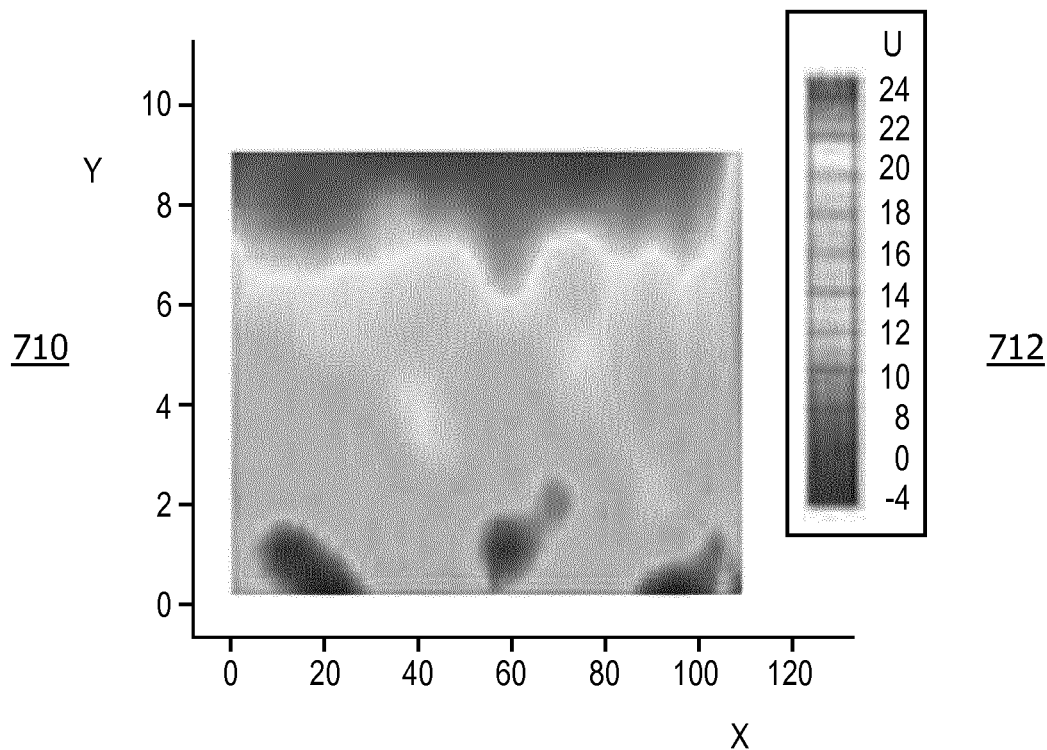
FIG. 7B is a view of color-coded 2-dimensional (planar) representation of a quantified cortical malformation, in accordance with a representative embodiment of the present disclosure.

In the process of FIG. 2 described above, the mapping at S250 is performed before the color coding at S260. However, the mapping may be performed after the color coding. Additionally, the process may be reversed so that instead of the 2-dimensional values being mapped to the 3-dimensional mesh, the 3-dimensional mesh is mapped to the 2-dimensional values. That is, in an embodiment, the cortical surface with color-coded malformations can be parameterized in spherical coordinates and mapped to a planar rectangle for ease of viewing. The mapping of the 3-dimensional mesh to the 2-dimensional surface is straightforward, and is analogous to mapping a globe to a map as in FIG. 7A, but results in a 2-dimensional map such as the example illustrating the concept in FIG. 7B. That is, FIG. 7A is a view of an illustrative mapping transformation to map a 3-dimensional spherical surface to a planar rectangle, and FIG. 7b is a view of a color-coded 2-dimensional (planar) representation of a quantified cortical malformation, in accordance with a representative embodiment of the present disclosure.

In FIG. 2, several of the processes can be performed automatically based on the pre-surgical magnetic resonance imaging scan. For example, S220, S230, S240, S250, S260 and S270 may be performed automatically using, for example, computers and computer algorithms run in accordance with computer software executed by a processor. The operations at S220, S230, S240, S250, S260 and S270 may be performed automatically as a group, individually, or in groups of one or more but less than all of the operations. Thus, the processes shown in FIG. 2 provide for automatic detection of cortical malformations, quantitative evaluation of the cortical malformations, and color-coded representation of the cortical malformations such as via a function of shape.

Additionally, the processes in FIG. 2 at S220, S230, S240, S250 and S260 may be performed by the same magnetic resonance imaging system that performs the pre-surgical scan at S210. Alternatively, the processes in FIG. 2 at S220, S230, S240, S250 and S260 may be performed by one or more different computers directly indirectly connected (over a network) or not connected at all to the magnetic resonance imaging system that performs the pre-surgical scan at S210. Processes described herein may be performed by modifying existing magnetic resonance products and imaging hardware. Further, additional research may be performed as a result of the output of the processes shown in FIG. 2, such as by using cortical descriptors that describe differentiated cortical malformations as imaging "biomarkers" of pathology.

Figure 3:
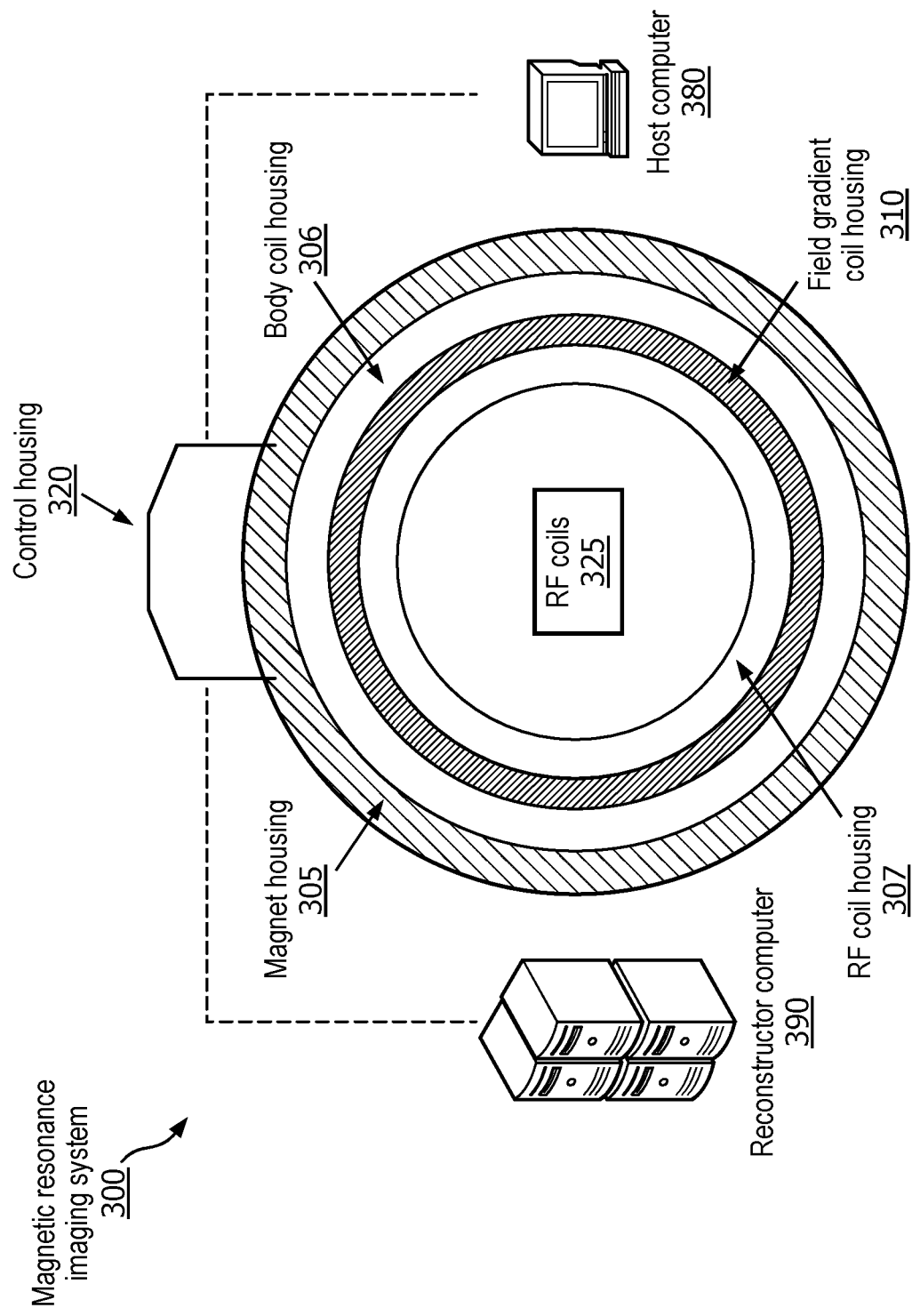
FIG. 3 is a view of an MRI system for cortical malformation identification, in accordance with a representative embodiment of the present disclosure.

FIG. 3 is a view of an MRI system for cortical malformation identification, in accordance with a representative embodiment of the present disclosure. In FIG. 3, a magnet housing 305 is designated with a hatch pattern as an outer structure of a magnetic resonance imaging system 300. A body coil housing 306 is immediately interior to the magnet housing 305. A field gradient coil housing 310 is immediately interior to the body coil housing 306. A radio frequency (RF) coil housing 307 is immediately interior to the field gradient coil housing 310. A control housing 320 is provided on the magnet housing 305 to house, e.g., external circuitry such as a transceiver.

In FIG. 3, radio frequency coils 325 are body coils placed on the body of the patient/subject who is subjected to the magnetic resonance imaging scan at S205. The radio frequency signals are emitted from the magnetic resonance imaging system 300 to excite the hydrogen atoms, and the hydrogen atoms emanate a weak radio frequency signal. The radio frequency signals from the hydrogen atoms are the signals with the intensity that is reflected in the image created by the magnetic resonance imaging system 300.

Figure 8:
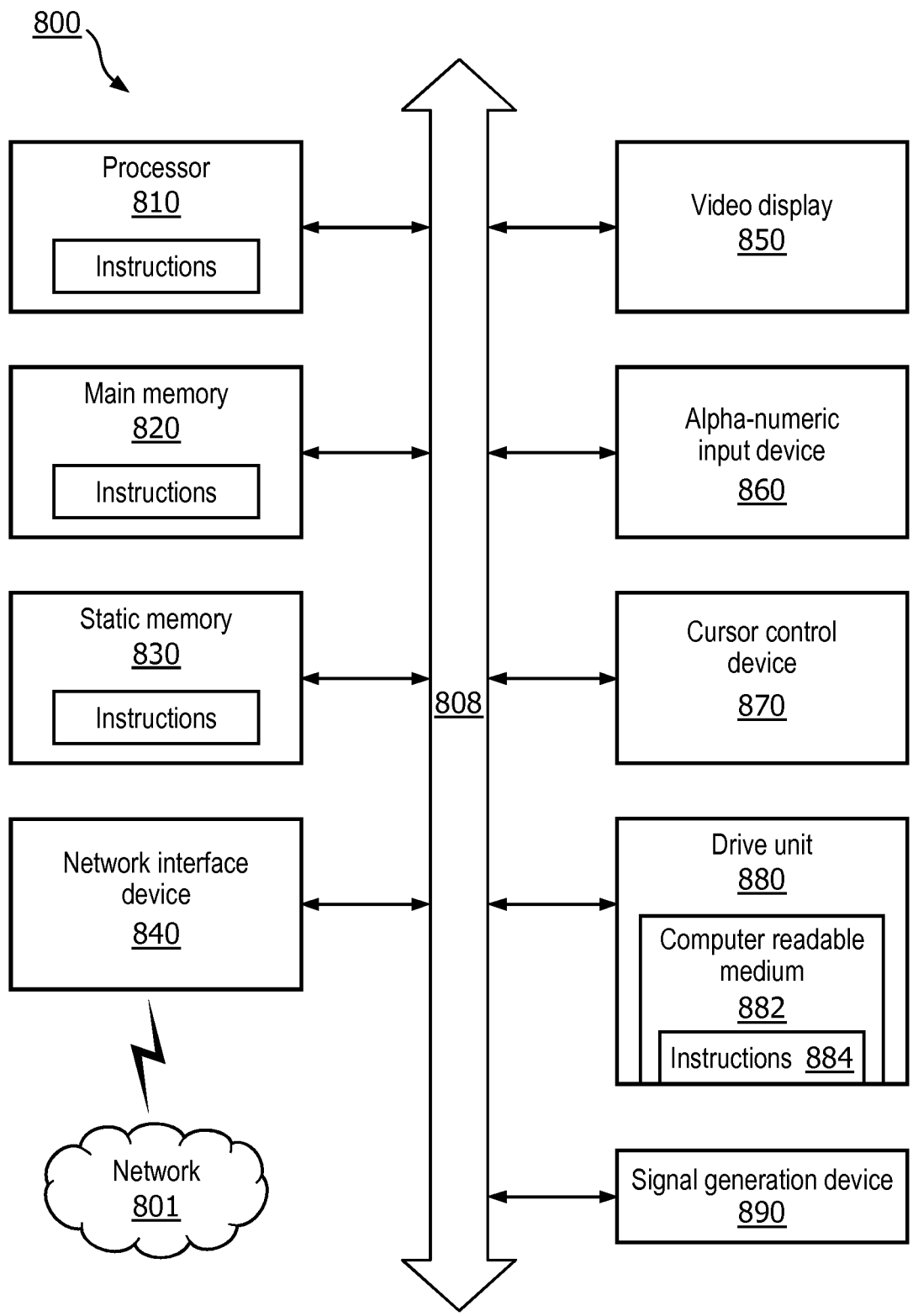
FIG. 8 is a view of an exemplary general computer system that includes a set of instructions for cortical malformation identification, in accordance with a representative embodiment of the present disclosure.

In FIG. 3, two computers included with the magnetic resonance imaging system 300 include the reconstructor computer 390 and the host computer 380. The host computer 380 interfaces with an operator of the magnetic resonance imaging system 300 to control the magnetic resonance imaging system 300 and to collect the images. The reconstructor computer 390 is a "background" computer that acts as a gatekeeper for data flow. The reconstructor computer 390 does not interact with the operator. Although not shown in FIG. 3, data may also be taken offline so that analysis may be performed on a, for example desktop, computer using software that may be proprietary to the manufacturer of the magnetic resonance imaging system 300. FIG. 8 shows a general computer system that may partially or fully be used to implement the reconstructor computer 390 and host computer 380, as well as any other computer or computing device that performs part or all of methods described herein.

FIG. 8 is a view of an exemplary general computer system that includes a set of instructions for cortical malformation identification, in accordance with a representative embodiment of the present disclosure. FIG. 8 is an illustrative embodiment of a general computer system, on which a method of cortical malformation identification can be implemented, and which is shown and is designated 800. The computer system 800 can include a set of instructions that can be executed to cause the computer system 800 to perform any one or more of the methods or computer based functions disclosed herein. The computer system 800 may operate as a standalone device or may be connected, for example, using a network 801, to other computer systems or peripheral devices.

In a networked deployment, the computer system 800 may operate in the capacity of a server or as a client user computer in a server-client user network environment, or as a peer computer system in a peer-to-peer (or distributed) network environment. The computer system 800 can also be implemented as or incorporated into various devices, such as a stationary computer, a mobile computer, a personal computer (PC), a laptop computer, a tablet computer, a wireless smart phone, a communications device, a control system, a web appliance, a reconstructor computer, a host computer, or any other machine capable of executing a set of instructions (sequential or otherwise) that specify actions to be taken by that machine. The computer system 800 can be incorporated as or in a particular device that in turn is in an integrated system that includes additional devices. In a particular embodiment, the computer system 800 can be implemented using electronic devices that provide video and/or data communication. Further, while a single computer system 800 is illustrated, the term "system" shall also be taken to include any collection of systems or sub-systems that individually or jointly execute a set, or multiple sets, of instructions to perform one or more computer functions.

As illustrated in FIG. 8, the computer system 800 includes a processor 810. A processor for a computer system 800 is tangible and non-transitory. As used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. A processor is an article of manufacture and/or a machine component. A processor for a computer system 800 is configured to execute software instructions in order to perform functions as described in the various embodiments herein. A processor for a computer system 800 may be a general-purpose processor or may be part of an application specific integrated circuit (ASIC). A processor for a computer system 800 may also be a microprocessor, a microcomputer, a processor chip, a controller, a microcontroller, a digital signal processor (DSP), a state machine, or a programmable logic device. A processor for a computer system 800 may also be a logical circuit, including a programmable gate array (PGA) such as a field programmable gate array (FPGA), or another type of circuit that includes discrete gate and/or transistor logic. A processor for a computer system 800 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 800 includes a main memory 820 and a static memory 830 that can communicate with each other via a bus 808. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 800 may further include a video display unit 850, such as a liquid crystal display (LCD), an organic light emitting diode (OLED), a flat panel display, a solid state display, or a cathode ray tube (CRT). Additionally, the computer system 800 may include an input device 860, such as a keyboard/virtual keyboard or touch-sensitive input screen or speech input with speech recognition, and a cursor control device 870, such as a mouse or touch-sensitive input screen or pad. The computer system 800 can also include a disk drive unit 880, a signal generation device 890, such as a speaker or remote control, and a network interface device 840.

In a particular embodiment, as depicted in FIG. 8, the disk drive unit 880 may include a computer-readable medium 882 in which one or more sets of instructions 884, e.g. software, can be embedded. Sets of instructions 884 can be read from the computer-readable medium 882. Further, the instructions 884, when executed by a processor, can be used to perform one or more of the methods and processes as described herein. In a particular embodiment, the instructions 884 may reside completely, or at least partially, within the main memory 820, the static memory 830, and/or within the processor 810 during execution by the computer system 800.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 882 that includes instructions 884 or receives and executes instructions 884 responsive to a propagated signal; so that a device connected to a network 801 can communicate voice, video or data over the network 801. Further, the instructions 884 may be transmitted or received over the network 801 via the network interface device 840.

Notably, computers in or around the immediate vicinity of a magnetic resonance imaging system 300 (or 900 described below), may vary from typical computers to ensure they do not interfere with the operation of the magnetic resonance imaging system 300 or 900. For example, a computer system 800 may be modified to ensure that it emits no or negligible magnetic or radio frequency transmissions.

Figure 9:
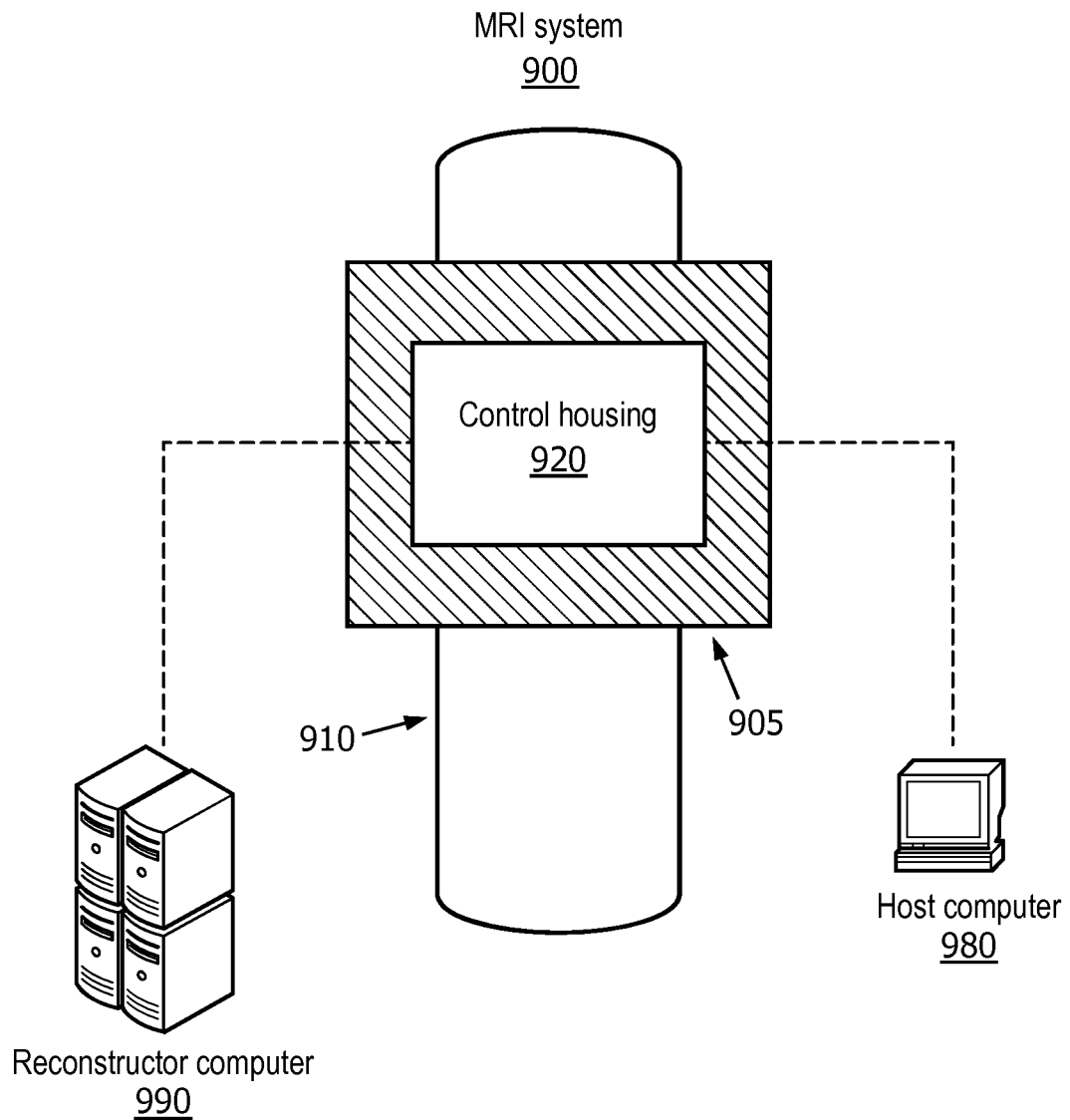
FIG. 9 is another view of an MRI system for cortical malformation identification, in accordance with a representative embodiment of the present disclosure.

FIG. 9 is another view of an MRI system for cortical malformation identification, in accordance with a representative embodiment of the present disclosure. In FIG. 9, an overhead view of the magnetic resonance imaging system 900 shows the table 910 that passes through the core 905 of the magnetic resonance imaging system 900. A control housing 920 on top of the magnetic resonance imaging system 900 may initially generate the greyscale image that is based on the signal intensities of the received radio frequency signals from the patient/subject.

In FIG. 9, the reconstructor computer 990 is shown separated from the main portion of the magnetic resonance imaging system 900. However, the reconstructor computer 990 may be built-in, hidden from view, remotely connected, or otherwise configured insofar as the reconstructor computer 990 may not be intended to interface with the operator of the magnetic resonance imaging system 900. On the other hand, host computer 980 interfaces with the operator of the magnetic resonance imaging system 900, such as by receiving instructions for a transmission sequence or by receiving data of the patient/subject to be imaged.

Figure 10:
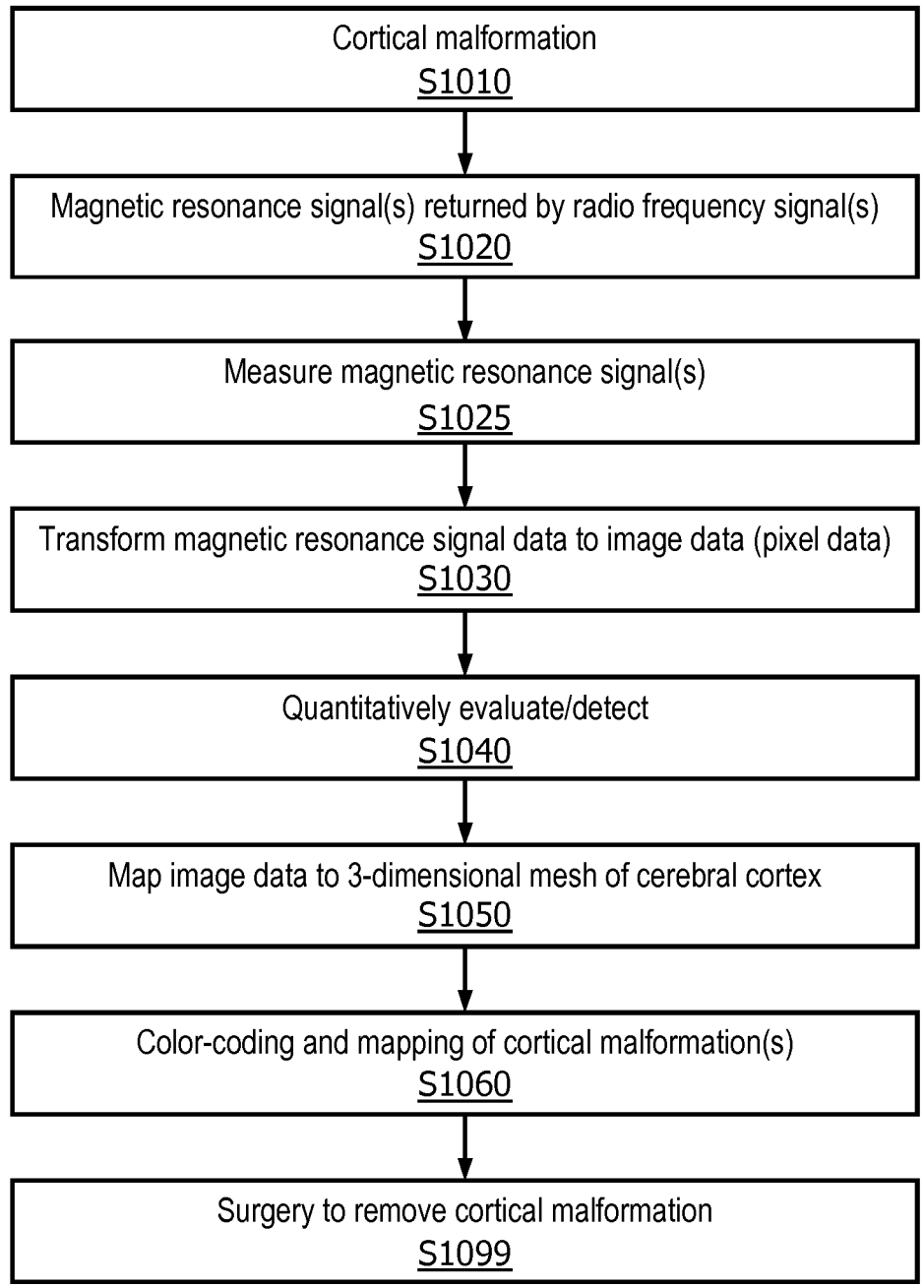
FIG. 10 is a view of another process for cortical malformation identification, in accordance with a representative embodiment of the present disclosure.

FIG. 10 is a view of another process for cortical malformation identification, in accordance with a representative embodiment of the present disclosure. At S1010, the cortical malformation exists. At S1020, during the magnetic resonance imaging scan, magnetic resonance imaging signals are returned by radio frequency signals from the patient/subject. At S1025, the returned radio frequency signals are measured. At S1030, the magnetic resonance imaging signal data obtained from the measurements is transformed to image data to produce the greyscale image. At S1040, the image data is quantitatively evaluated and used to detect the cortical malformation. At S1050, the image data is mapped to a 3-dimensional mesh of the cerebral cortex that is also obtained from the magnetic resonance imaging scan. At S1060, the image data mapped to the 3-dimensional mesh is colorized. At S1099, surgery is performed to remove the cortical malformation.

The process of FIG. 10 shows the variety of transformations that occur in or using cortical malformation identification. For example, a cortical malformation that exists at S1010 is removed at S1099. A radio frequency signal returned at S1010 is transformed to image data at S1030. Furthermore, cortical malformations detected in the image data are mapped on a 3-dimensional mesh and parametrized and further mapped on a 2-dimensional plane at S1050, and colorized at S1060.

The FIG. 10 shows a variety of transformations that can occur using the full teachings described herein. However, a subset of these teachings may be individually combined to still produce a new and useful result. For example, the quantitative evaluation/analysis and the automatic detection alone produces a useful identification of a cortical malformation. As such, the application of such a result to both a 3-dimensional mesh, as well as the color coding of the 2-dimensional image data that results from the evaluation/analysis, can each individually be considered separately new and useful applications of the concepts described herein.

Accordingly, cortical malformation identification enables proper identification of a variety of congenital conditions that may appear via cortical malformations in a patient/subject. The measurement of signal intensity from magnetic resonance imaging systems can be expanded from producing greyscale images to analyzing the underlying abnormalities to be addressed.

Insofar as there are several types of cortical malformations and the result is seizures, the cortical malformation identification described herein will assist in both diagnosing and remedying a variety of seizure-inducing maladies. The accurate localization and delineation of cortical malformations as described herein will closely correlate patient/subject outcome with the success of surgical resection, i.e., by removing all abnormal seizure brain tissue and leaving the brain tissue that is normal.

The color-coding as an assistance tool allows a medical professional to match the color-coded image (physical or electronic) showing the cortical malformation with the actual anatomy of the patient. Since the actual anatomy of the patient/subject itself does not provide an easy way to identify the cortical malformation visually, the success of surgeries in an operating room can be measurably improved using the cortical malformation identification described herein. The method can identify cortical malformations in a pre-operative magnetic resonance imaging scan of a patient, and the resultant color coded 2-dimensional image can be registered with the patient's anatomy during the intervention for surgical guidance and optimal tissue resection. Furthermore, color-coding can be included and provided in reports to patients as an intuitive illustration of their condition and affected brain location.

Although cortical malformation identification has been described with reference to several exemplary embodiments, it is understood that the words that have been used are words of description and illustration, rather than words of limitation. Changes may be made within the purview of the appended claims, as presently stated and as amended, without departing from the scope and spirit of cortical malformation identification in its aspects.

Although cortical malformation identification has been described with reference to particular means, materials and embodiments, cortical malformation identification is not intended to be limited to the particulars disclosed; rather cortical malformation identification extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the Figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

According to an aspect of the present disclosure, a cortical malformation identification method includes performing a magnetic resonance imaging (MRI) scan of the brain. The method includes obtaining digital image data from the magnetic resonance imaging scan. The method also includes quantitatively evaluating the digital image data to produce quantified scan data, and automatically detecting a cortical malformation based on the quantified scan data. The quantified scan data is mapped to a 3-dimensional mesh representation of the cerebral cortex. The method further includes color-coding of the 3-dimensional mesh representation of the cerebral cortex so that the cortical malformation is identified and shown on the mesh in a different color than the remainder of the healthy cerebral cortex. The color-coded mapped image of the cerebral cortex is output, for example by a printer or via a digital electronic screen.

According to another aspect of the present disclosure, a cortical malformation identification method includes quantitatively evaluating, using a processor of a computer that includes the processor and a memory, digital image data from a magnetic resonance imaging (MRI) scan on a cerebral cortex to produce quantified scan data. The method also includes automatically detecting a cortical malformation based on the quantified scan data. An image of the cerebral cortex is color coded so that the cortical malformation is shown in a different color than the remainder of the cerebral cortex in the image, based on the quantified scan data.

According to yet another aspect of the present disclosure, the method further includes measuring the cortical malformation based on the quantified scan data and color-coded image to produce measurements of the cortical malformation.

According to still another aspect of the present disclosure, the method also includes automatically diagnosing one of a plurality of congenital conditions based on the quantified scan data and the measurements.

According to another aspect of the present disclosure, the color-coding includes color-coding different sections of the image of the cerebral cortex based on the quantified scan data. The different color-coded sections of the cerebral cortex are registered with an anatomy of the cerebral cortex in an operating room. The image is color-coded to visually delineate a portion of the cortical malformation to be removed by surgery.

According to yet another aspect of the present disclosure, the diagnosed congenital condition is a cortical malformation. The cortical malformation may be one of Taylor's focal cortical dysplasia, architectural dysplasia, and/or cytoarchitectural dysplasia.

According to still another aspect of the present disclosure, the color-coded image of the cerebral cortex is displayed via an electronic display in an operating room in which the cortical malformation is removed by the surgery.

According to another aspect of the present disclosure, the method also includes deriving an index from the quantitative evaluation of the cortical malformation to differentiate a disease type of the cortical malformation.

According to yet another aspect of the present disclosure, the method further includes automatically performing deformable segmentation to segment the cerebral cortex in a 3-dimensional representation of the cerebral cortex in the magnetic resonance imaging scan without user interaction.

According to still another aspect of the present disclosure, the method also includes classifying tissue of the cerebral cortex based on the quantified scan data obtained using the deformable segmentation in the magnetic resonance imaging scan.

According to another aspect of the present disclosure, the method also includes generating a representation of an inner cortical surface and an outer cortical surface as a 3-dimensional triangular mesh of hemispheres of the cerebral cortex. An inner boundary and an outer boundary of the cerebral cortex are represented as similar triangular surfaces of the 3-dimensional triangular mesh.

According to yet another aspect of the present disclosure, the quantified scan data includes measurements of signal intensity measured during the magnetic resonance imaging scan. The signal intensity is representable as a pixel value in an image based on the digital image data.

According to still another aspect of the present disclosure, the quantified scan data includes an average value of signal intensity for signals normal to, and pointing inward from an inner cortical surface of the cerebral cortex and outward from an outer cortical surface of the cerebral cortex, respectively.

According to another aspect of the present disclosure, the method also includes mapping the quantified scan data to triangular meshes representing an inner cortical surface and an outer cortical surface of the cerebral cortex.

According to yet another aspect of the present disclosure, the method further includes comparing 3-dimensional surfaces from different cerebral cortexes in the same parametric space defined by triangular meshes of inner cortical surfaces and outer cortical surfaces of the different cerebral cortexes to correlate quantified scan data of the different cerebral cortexes.

According to still another aspect of the present disclosure, the cortical malformation is detected by identifying a deviation in quantified scan data between left and right sides of the cerebral cortex.

According to another aspect of the present disclosure, a cortical malformation identification method includes quantitatively evaluating, using a processor of a computer that includes the processor and a memory, digital image data from a magnetic resonance imaging (MRI) scan on a cerebral cortex to produce quantified scan data. The method also includes automatically detecting a cortical malformation based on the quantified scan data. The method further includes mapping a 3-dimensional representation of the cerebral cortex to the quantified scan data to produce a mapped image of the cerebral cortex including the detected cortical malformation.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A cortical malformation identification method, comprising:
   performing a magnetic resonance imaging (MRI) scan on a cerebral cortex;
   obtaining digital image data from the MRI scan;
   generating, from the digital image data, a representation of an inner cortical surface and an outer cortical surface as a three-dimensional triangular mesh of hemispheres of the cerebral cortex, wherein an inner boundary and an outer boundary of the cerebral cortex are represented as similar triangular surfaces of the three-dimensional triangular mesh;
   quantitatively evaluating the representation of the cerebral cortex to produce quantified scan data comprising measurements of signal intensity measured during the MRI scan, wherein the signal intensity is represented in one or more of pixel or voxel values in images based on the digital image data, the signal intensity of the quantified scan data further comprising an average value of signal intensity for signals respectively normal to, and pointing inward from, an inner cortical surface of the cerebral cortex and pointing outward from an outer cortical surface of the cerebral cortex;
   automatically detecting a cortical malformation based on the quantified scan data;
   mapping a three-dimensional representation of the cerebral cortex to the quantified scan data to produce a mapped image of the cerebral cortex;
   color-coding the mapped image of the cerebral cortex so that the cortical malformation is shown in a different color than a remainder of the cerebral cortex in the mapped image; and
   outputting the color-coded mapped image of the cerebral cortex.

2. A medical resonance imaging (MRI) system for cortical malformation identification, comprising:
   a processor;
   a memory that stores instructions, which when executed by the processor, causes the processor to:
   generate, from digital image data from an MRI scan on a cerebral cortex, a representation of an inner cortical surface and an outer cortical surface as a three-dimensional triangular mesh of hemispheres of the cerebral cortex, wherein an inner boundary and an outer boundary of the cerebral cortex are represented as similar triangular surfaces of the three-dimensional triangular mesh;
   quantitatively evaluate the representation of the cerebral cortex to produce quantified scan data comprising measurements of signal intensity measured during the MRI scan, wherein the signal intensity is represented in one or more of pixel or voxel values in images based on the digital image data, the signal intensity of the quantified scan data further comprising an average value of signal intensity for signals respectively normal to, and pointing inward from, an inner cortical surface of the cerebral cortex and pointing outward from an outer cortical surface of the cerebral cortex;
   automatically detect a cortical malformation based on the quantified scan data; and
   color-code a mapped image of the cerebral cortex so that the cortical malformation is shown in a different color than a remainder of the cerebral cortex in the mapped image, based on the quantified scan data.

3. The MRI system for cortical malformation identification of claim 2, wherein the instructions further cause the processor to:
   measure the cortical malformation based on the quantified scan data and color-coded image to produce measurements of the cortical malformation.

4. The MRI system for cortical malformation identification of claim 3, wherein the instructions further cause the processor to:
   automatically diagnose one of a plurality of congenital conditions based on the quantified scan data and the measurements to produce a diagnosed congenital condition.

5. The MRI system for cortical malformation identification of claim 4, wherein the diagnosed congenital condition is a cortical malformation comprising one of Taylor's focal cortical dysplasia, architectural dysplasia, or cytoarchitectural dysplasia.

6. The MRI system for cortical malformation identification of claim 2, wherein the color-coded mapped image comprises color-coding different sections of the image of the cerebral cortex based on the quantified scan data;
   the different color-coded sections of the cerebral cortex are registered with an anatomy of the cerebral cortex in an operating room; and
   the image is color-coded to visually delineate a portion of the cortical malformation to be removed by surgery.

7. The MRI system for cortical malformation identification of claim 2, wherein the color-coded image of the cerebral cortex is displayed via an electronic display in an operating room in which the cortical malformation is removed by surgery.

8. The MRI system for cortical malformation identification of claim 2, wherein the instructions further cause the processor to:

derive an index from the quantitative evaluation of the cortical malformation to differentiate a disease type of the cortical malformation.

9. The MRI system for cortical malformation identification of claim 2, wherein the instructions further cause the processor to:
automatically perform deformable segmentation to segment the cerebral cortex in a three-dimensional representation of the cerebral cortex in the MRI scan without user interaction.

10. The MRI system for cortical malformation identification of claim 9, wherein the instructions further cause the processor to:
classify tissue of the cerebral cortex based on the quantified scan data obtained using the deformable segmentation in the MM scan.

11. The MRI system for cortical malformation identification of claim 2, wherein the quantified scan data comprises measurements of signal intensity measured during the MRI scan, wherein the signal intensity is represented as pixel values in images based on the digital image data.

12. The MRI system for cortical malformation identification of claim 2, wherein the instructions further cause the processor to:
map the quantified scan data to triangular meshes representing an inner cortical surface and an outer cortical surface of the cerebral cortex.

13. The MRI system for cortical malformation identification of claim 2, wherein the instructions further cause the processor to:
compare three dimensional surfaces from different cerebral cortexes in the same parametric space defined by triangular meshes of inner cortical surfaces and outer cortical surfaces of the different cerebral cortexes to correlate quantified scan data of the different cerebral cortexes.

14. The MRI system for cortical malformation identification of claim 2, wherein the cortical malformation is detected by identifying a deviation in quantified scan data between left and right sides of the cerebral cortex.

15. A medical resonance imaging (MRI) system for cortical malformation identification, comprising:
a processor;
a memory that stores instructions, which when executed by the processor, causes the processor to:
quantitatively evaluate digital image data from a magnetic resonance imaging (MRI) scan on a cerebral cortex to produce quantified scan data comprising measurements of signal intensity measured during the MRI scan, wherein the signal intensity is represented in one or more of pixel or voxel values in images based on the digital image data, wherein the digital image data comprises a representation of an inner cortical surface and an outer cortical surface as a three-dimensional triangular mesh of hemispheres of the cerebral cortex and an inner boundary and an outer boundary of the cerebral cortex are represented as similar triangular surfaces of the three-dimensional triangular mesh, the signal intensity of the quantified scan data further comprising an average value of signal intensity for signals respectively normal to, and pointing inward from, an inner cortical surface of the cerebral cortex and pointing outward from an outer cortical surface of the cerebral cortex;
automatically detect a cortical malformation based on the quantified scan data; and
map a three-dimensional representation of the cerebral cortex to the quantified scan data to produce a mapped image of the cerebral cortex including the detected cortical malformation.

16. The MRI system for cortical malformation identification of claim 15, wherein the instructions further cause the processor to:
perform the MRI scan on the cerebral cortex;
obtain the digital image data from the MRI scan;
map a three-dimensional representation of the cerebral cortex to the quantified scan data to produce the mapped image of the cerebral cortex; and
output the color-coded mapped image of the cerebral cortex.

17. The MRI system for cortical malformation identification of claim 16, wherein the instructions further cause the processor to:
automatically diagnose one of a plurality of congenital conditions based on the quantified scan data and the measurements the signal intensity to produce a diagnosed congenital condition.

18. The MRI system for cortical malformation identification of claim 17, wherein the diagnosed congenital condition is a cortical malformation comprising one of Taylor's focal cortical dysplasia, architectural dysplasia, or cytoarchitectural dysplasia.

* * * * *